(12) United States Patent
Wei

(10) Patent No.: US 6,572,229 B2
(45) Date of Patent: Jun. 3, 2003

(54) BACK PROJECTION VISUAL FIELD TESTER

(75) Inventor: Jay Wei, Fremont, CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/884,507

(22) Filed: Jun. 14, 2001

(65) Prior Publication Data

US 2003/0007128 A1 Jan. 9, 2003

(51) Int. Cl.[7] ................................. A61B 3/10
(52) U.S. Cl. ...................................... 351/211
(58) Field of Search ......................... 351/200, 205, 351/211, 221, 222, 224, 226, 237, 239–243; 359/443, 445, 456, 457, 460, 451

(56) References Cited

U.S. PATENT DOCUMENTS

| | | | | |
|---|---|---|---|---|
| 4,361,382 A | * | 11/1982 | Miyoshi et al. | 359/453 |
| 4,626,090 A | * | 12/1986 | Charlier et al. | 351/226 |
| 5,024,519 A | * | 6/1991 | Howard et al. | 351/224 |
| 5,046,835 A | * | 9/1991 | Billeter et al. | 351/224 |
| 5,323,194 A | | 6/1994 | Campbell et al. | 351/226 |
| 5,459,536 A | * | 10/1995 | Shalon et al. | 351/224 |
| 5,461,436 A | * | 10/1995 | Campbell | 351/224 |
| 5,717,481 A | * | 2/1998 | Obata et al. | 351/224 |
| 5,870,169 A | | 2/1999 | Koest | 351/225 |
| 6,139,150 A | | 10/2000 | Wei | 351/211 |
| 6,315,412 B1 | * | 11/2001 | Snodderly et al. | 351/200 |
| 6,347,012 B1 | * | 2/2002 | Monson et al. | 359/451 |
| 6,414,727 B1 | * | 7/2002 | Benton | 359/443 |

* cited by examiner

Primary Examiner—George Manuel
Assistant Examiner—John R. Sanders
(74) Attorney, Agent, or Firm—Michael B. Einschlag

(57) ABSTRACT

One embodiment of the present invention is a visual field tester that includes: (a) a projection screen; (b) a stimulus projection system that projects a light source onto a first side of the projection screen; (c) a background projection system that projects a background light onto the first side of the projection screen; and (d) a magnifier lens system disposed on a second side of the projection screen that directs light transmitted through the projection screen to a predetermined location.

17 Claims, 3 Drawing Sheets

BACK PROJECTION VISUAL FIELD TESTER

TECHNICAL FIELD OF THE INVENTION

The present invention pertains to an optical device for visual field testing. In particular, the present invention relates to an apparatus for visual field testing using a back projection system.

BACKGROUND OF THE INVENTION

A visual field tester is an apparatus that is used to test, among other things, the peripheral vision of a human eye—such apparatus have been known in the art for many years. Test results from visual field testers are used to diagnosis diseases that cause degradation of vision sensitivity. For example, a Standard Automated Perimeter (SAP), one of the most accepted of testing apparatus, typically performs brightness contrast sensitivity tests over a large visual field.

In prior art visual field testers used to perform a contrast sensitivity test, it is common to include a hemispherical projection surface and a stimulus optical projection system. In a typical such visual field tester, the hemispherical projection surface is uniformly illuminated (for example, using a white light source) to provide a constant and uniform background illumination—the aim is that the hemispherical projection surface be a Lambertian illumination surface (i.e., a surface upon which brightness is constant over different viewing angles). In a typical such visual field tester, the stimulus optical projection system presents stimuli (typically in the form of a circular spot) at selected points on an internal surface of the hemispherical projection surface. For example, this is done by sequentially flashing images of light sources on the internal surface of the hemispherical projection surface where the position and brightness of the stimuli are specified by a computer implemented algorithm. In use for testing, a patient's eye is placed at, or close, to the center of the hemispherical projection surface, and the patient is asked to respond to the stimuli by pressing, for example, a mouse button. Then, the contrast sensitivity of the patient's visual field is mapped by changing the brightness and position of the stimuli on the constant, uniform background illumination. However, such prior art devices have a drawback in that they are bulky and expensive. In particular, the radius of the hemispherical projection surface is typically set to about 30 cm to enable the patient to see the stimulus comfortably (i.e., without straining the patient's test eye).

U.S. Pat. No. 5,870,169 (the '169 patent) discloses a visual field tester that utilizes a hemispherical surface in an alternative manner to that described above. Specifically, instead of projecting a stimulus onto an internal surface of a hemispherical projection surface from the patient's side, as disclosed in the '169 patent, a rear projection device is used to project a stimulus onto an external surface of a hemispherical projection surface. In this case, the hemispherical projection surface is comprised of a transparent material, and the patient can see the stimulus when it is viewed from the interior surface of the hemispherical projection surface. The apparatus in the '169 patent provides a stimulus having an improved shape and brightness uniformity over the apparatus's 72-degree visual field when compared with the shape and brightness uniformity of prior visual field testers. However, due to absorption by the transparent material, the maximum brightness of the stimulus is reduced.

An improved visual field tester is disclosed in U.S. Pat. No. 5,046,835 (the '835 patent). As disclosed in the '835 patent, the size of a visual field tester can be reduced by using a cupola-less optical system. In particular, the '835 patent discloses a direct viewing optical system that projects a stimulus directly into a patient's eye. To do this, the optical system images a light source onto an intermediate image plane of an eyepiece (to serve as a stimulus), and separately images light output from a diffused light source onto the intermediate image plane (to serve as a uniformly illuminated background). Then, the stimulus and the background are combined through a beamsplitter, and projected onto the patient's retina. In use, the patient views a test field through large field of view (60 degrees), long working-distance eyepieces. Because the apparatus disclosed in the '835 patent does not utilize a hemispherical projection surface, the size of the apparatus is significantly reduced. However, the cost of a large field of view, long working-distance eyepiece is increased due the aperture size of the lens.

U.S. Pat. No. 6,139,150 discloses a visual field tester that eliminates use of an eyepiece. As a result, the visual field tester has reduced cost and complexity when compared with the above-described apparatus.

In light of the above, there is a need in the art for further visual field testers that can, for example, provide an SAP test in a cost-effective way.

SUMMARY OF THE INVENTION

Embodiments of the present invention advantageously satisfy the above-identified need in the art, and provide a back projection visual field tester. Specifically, one embodiment of the present invention is a visual field tester that comprises: (a) a projection screen; (b) a stimulus projection system that projects a light source onto a first side of the projection screen; (c) a background projection system that projects a background light onto the first side of the projection screen; and (d) a magnifier lens system, disposed on a second side of the projection screen, that directs light transmitted through the projection screen to a predetermined location.

DETAILED DESCRIPTION

Figure 1:
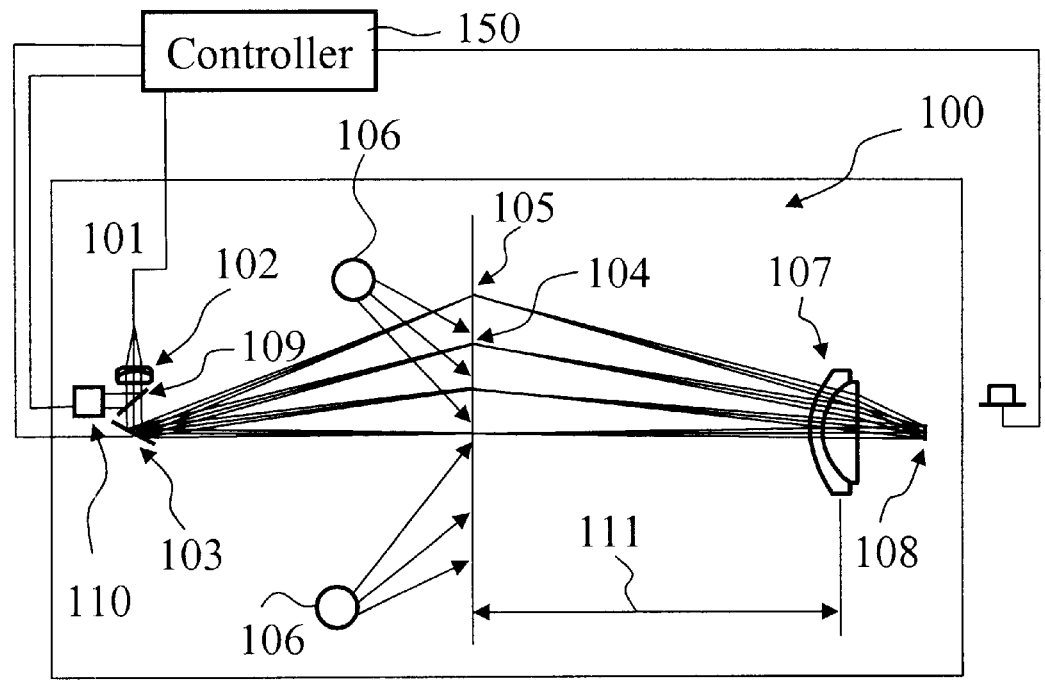
FIG. 1 shows a block diagram of a preferred embodiment of a back projection visual field tester that is fabricated in accordance with the present invention.

FIG. 1 shows a block diagram of back projection visual field tester 100 that is fabricated in accordance with a preferred embodiment of the present invention. As shown in FIG. 1, a stimulus projection system for back projection visual field tester 100 comprises light source 101 and stimulus projection lens system 102 (although stimulus projection lens system 102 is shown as being comprised of one lens, those of ordinary skill in the art will readily understand that stimulus projection lens system 102 may comprise one or more lenses). In use, an aperture of light source 101 is imaged by stimulus projection lens system 102 onto projection screen 105 (an embodiment of projection screen 105 will be described below in conjunction with FIG. 3) to provide a stimulus (in FIG. 1, the stimulus is shown at various positions as stimuli 104 to illustrate that the stimulus may be presented to a patient at various positions on projection screen 105). Light source 101 may be an LED, a Halogen lamp, a short arc Mercury lamp, a Xenon lamp, a laser, or any other suitable light source. The shape of the stimulus may be circular (a typical visual field tester utilizes a circular spot), or it may be any other shape that can be set by utilizing an aperture for light source 101 in accordance with any one of a number of methods and apparatus that are well known to those of ordinary skill in the art. Further, the shape of the stimulus may be changed under the control of controller 150 (for example, a computer) by changing the aperture and/or its shape in accordance with any one of a number of methods and apparatus that are well known to those of ordinary skill in the art. Still further, an interface apparatus (not shown) is disposed between controller 150 and light source 101 in a manner which is well known to those of ordinary skill in the art. Then, in accordance with methods that are well known to those of ordinary skill in the art, for example, under software control, controller 150 sends signals through the interface to light source 101 to cause it to emit light. In accordance with methods that are well known to those of ordinary skill in the art, controller 150, under software control, controls output from light source 101 as to one or more of: (a) duration of illumination interval; (b) intensity of illumination during the illumination interval; and (c) even color. As further shown in FIG. 1, beamsplitter 109 is disposed in the optical path of the stimulus projection system and directs a portion of the light output from light source 101 to photodetector 110. Output from photodetector 109 is applied as input to controller 150, and controller 150 utilizes this input to monitor, among other things, the brightness of the stimulus.

As shown in FIG. 1, light passing through beamsplitter 109 impinges upon scanner system 103, and is directed by scanner system 103 to impinge on projection screen 105 at various positions. An interface apparatus (not shown) is disposed between controller 150 and scanner system 103 in a manner that is well known to those of ordinary skill in the art. Then, in accordance with methods that are well known to those of ordinary skill in the art, for example, under software control, controller 150 sends signals through the interface to scanner system 103 to cause scanner system to move and, thereby, to scan the light incident thereon over projection screen 105. As shown in FIG. 1, scanner system 103 comprises a gimbal-mounted mirror 103. Many methods are well known to those of ordinary skill in the art for use in fabricating a controller-controlled scanner, and in particular, a controller-controlled, gimbal-mounted mirror. For example, a suitable gimbal-mounted mirror apparatus is manufactured by the Newport Corporation of Irvine Calif.

As shown in FIG. 1, light source 106 uniformly illuminates projection screen 105 with light. Light source 106 may comprise white LEDs, tungsten lamps, Halogen lamps, and so forth. In some embodiments light source 106 may comprise a number of light sources, and in other embodiments it may comprise a light source in the form of, for example, a ring. In use then, projection screen 105 is uniformly illuminated: (a) by light from light source 106 and (b) by stimuli 104 where the (i) duration of an illumination interval; (ii) intensity of illumination during the illumination interval; and (iii) even color are set by controller 150 in accordance with predetermined criteria.

Projection screen 105 is viewed through a stimulus viewing system by a patient whose test eye is located at position 108 shown in FIG. 1. Position 108 is substantially at a center of a viewing box (not shown) which is, for example, a cone shaped enclosure. As shown in FIG. 1, the stimulus viewing system for back projection visual field tester 100 comprises magnifier lens system 107. Although magnifier lens system 107 is shown to be comprised of one lens, those of ordinary skill in the art will readily understand that magnifier lens system 107 may comprise one or more lenses.

In accordance with one embodiment of the present invention, the focal length of magnifier lens system 107 and physical distance 111 (i.e., the distance between projection screen 105 and magnifier lens system 107) are selected so that projection screen 105 is imaged at a distance about 30 cm away from the patient's test eye to reduce strain. In accordance with such an embodiment, an embodiment of back projection visual field tester 100 can be fabricated where the physical distance 111 between projection screen 105 and magnifier lens system 107 is much shorter than the 30 cm distance required for a patient to see comfortably. Advantageously, this enables the size of projection screen 105 and back projection visual field tester 100 to be substantially reduced over visual field testers fabricated in accordance with the prior art. To understand the magnitude of such a reduction, assume that distance 111 between projection screen 105 and magnifier lens system 107 is chosen to be 15 cm. In such a case, the total volume of the viewing optical space would be only ¼ of the volume if projection screen 105 were physically located 30 cm away from the patient's eye.

A visual field tester fabricated in accordance with one embodiment of the present invention may further comprise an apparatus for providing a fixation target or for fixing the position of a patient's test eye (such apparatus is not shown in FIG. 1 so that the operation of the remainder of the disclosed back projection visual field tester can more easily be understood). Such a fixation apparatus engages the attention of the test eye and may be fabricated in accordance with any one of a number of methods that are well known to those of ordinary skill in the art. For example, a fixation device may be an LED which is disposed at a predetermined location for viewing by the patient's test eye. Alternatively, a black dot can be painted on the center of projection screen 105 to serve as a fixation target during a central vision test. Further, a pair of black dots can be painted on both horizontal edges of projection screen 105 to serve as fixation targets during a peripheral vision test.

Lastly, as is well known to those of ordinary skill in the art, in order to fabricate a visual field tester in accordance with the present invention, the patient is provided with an apparatus for indicating the patient's perception of the presence or absence of optical radiation impinging upon the eye. As is well known, such indication apparatus may include a button which, when depressed, sends a signal to controller 150. Such an indication apparatus may also include foot pedals, mouses and the like. Lastly, controller 150 may be configured in accordance with any one of a number of methods that are well known to those of ordinary skill in the art to collect the patient's input to produce, as output, measurements of the patient's visual sensitivity.

Figure 2:
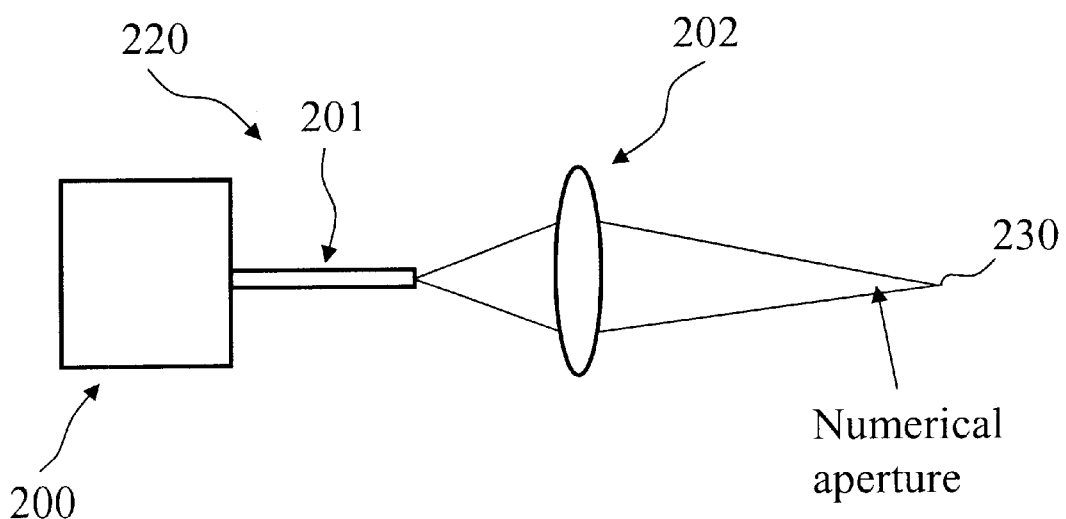
FIGS. 2 and 2A show block diagrams of a stimulus projection system that is fabricated in accordance with other embodiments of the present invention, which stimulus projection-system may replace the stimulus projection system shown in FIG. 1.

FIG. 2 shows a block diagram of stimulus projection system 220 that is fabricated in accordance with another embodiment of the present invention, which stimulus projection system 220 may replace the stimulus projection system comprised of light source 101 and stimulus projection lens system 102 shown in FIG. 1. As shown in FIG. 2, bright, white light source 200 (such as, for example, an arc lamp, a Halogen lamp, or any one of a number of other light sources that are well known to those of ordinary skill in the art) outputs light that is coupled into optical fiber 201, and light output from optical fiber 201 is transmitted, in turn, by stimulus projection lens system 202 to location 230 to form a stimulus. Although stimulus projection lens system 202 is shown as being comprised of one lens, those of ordinary skill in the art will readily understand that stimulation projection lens system 202 may comprise one or more lenses. In an alternative embodiment shown in FIG. 2A, stimulus projection system 228 may comprise white LED 210 (or other small emitting area light sources that are well known to those of ordinary skill in the art) in place of bright, white light source 200 and optical fiber 201.

Figure 2A:
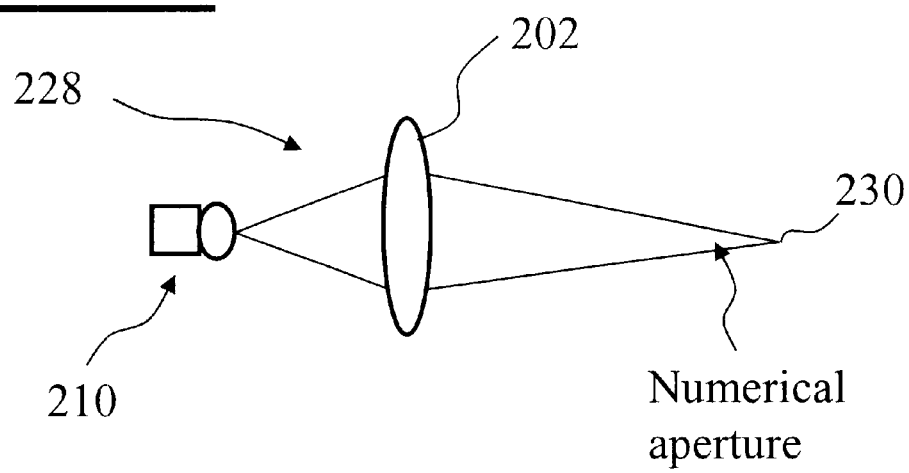

In accordance with one embodiment of the present invention, stimulus projection lens system 202 is designed to have such a long depth of focus that the image of a light aperture (for example, of optical fiber 201 shown in FIG. 2 or of LED 210 shown in FIG. 2A), i.e., the stimulus, is well focused over the entire area of projection screen 105. To do this, in accordance with one embodiment of the present invention, one makes the numerical aperture (i.e., the angle subtended from location 230 to projection lens system 202, as shown in FIGS. 2 and 2A) small enough to achieve the desired long depth of focus.

Figure 3:
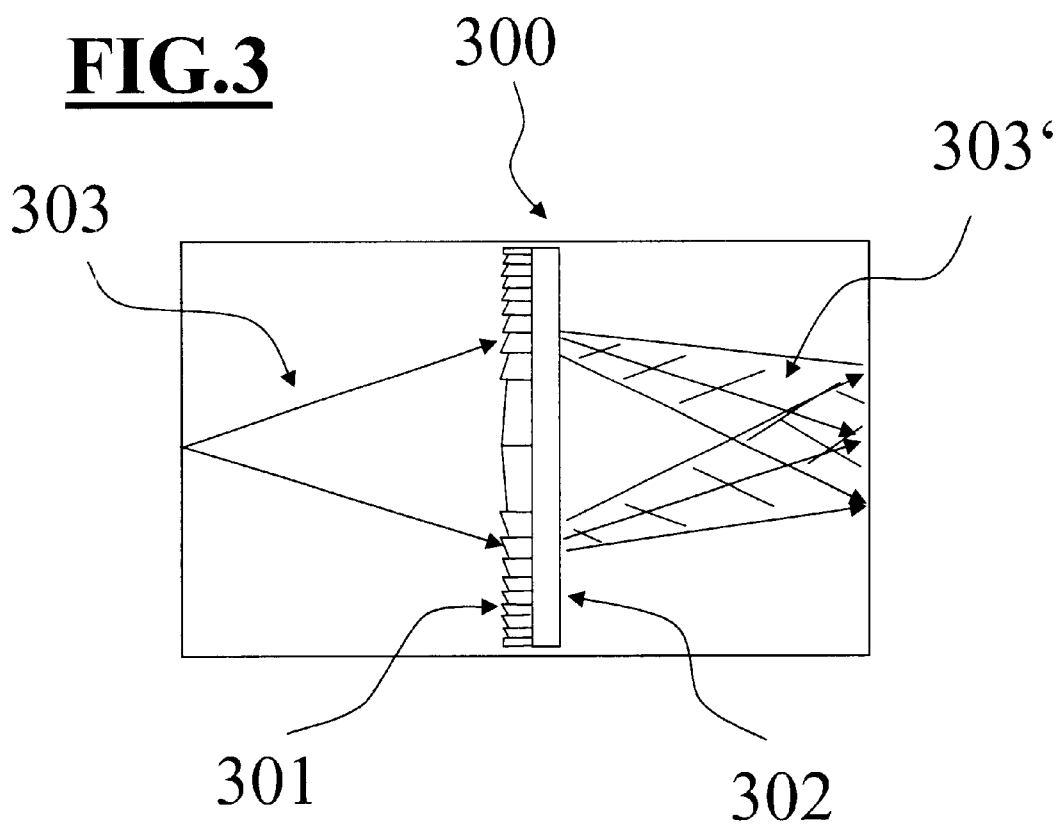
FIG. 3 shows a diagram of a preferred embodiment of a projection screen that is fabricated in accordance with the present invention for use in a back projection visual field tester that is fabricated in accordance with the present invention.

FIG. 3 shows a diagram of a preferred embodiment of projection screen 300 that is fabricated in accordance with the present invention for use in a back projection visual field tester that is fabricated in accordance with the present invention. In accordance with the present invention, projection screen 300 has two functions. In accordance with a first function of projection screen 300, projection screen 300 (by action of lens 301) acts as a lens. As such, projection screen 300 (by action of lens 301) directs optical beam 303 (representing light from the stimulus and from the background illumination) towards location 108 (as shown in FIG. 1) where the patient's test eye is placed. In accordance with a second function of projection screen 300, projection screen 300 (by action of diffuse light shaper 302) expands optical beam 303' (optical beam 303' is transmitted through projection screen 300) into a desired divergence angle. Because projection screen 300 is highly transparent (for example, it may be readily fabricated from a plastic material such as polycarbonate, polyseter, and the like), not much light is lost to absorption by the material of projection screen 300. In accordance with this embodiment of the present invention, the divergence angle of optical beam 303' is controlled so that optical beam 303' will substantially cover an aperture of magnifier lens system 107 (see FIG. 1). As a result, not much light will be vignetted by the aperture of magnifier lens system 107 (see FIG. 1). Since most of the light is directed into magnifier lens system 107 and, in turn, the patient's test eye, a high efficiency projection system is achieved. Such an embodiment of projection screen 300 can be fabricated by physically laminating two optical components together, namely, Fresnel lens 301 and light diffuser 302. Alternatively, projection screen 300 can be fabricated using a holographic method whereby a single piece of screen material can perform both functions, such a holographic diffuser is manufactured by the Physical Optics Corporation of Torrance, Calif.

In accordance with a further embodiment of the present invention, blue filters can be placed in the optical path of the stimulus projection system to generate a blue stimulus; and background illumination light source 106 can be either a yellow LED or a white light source covered with a yellow filter to generate a desired yellow background for a short-wavelength, standard automatic perimeter (SWAP) test.

Figure 4:
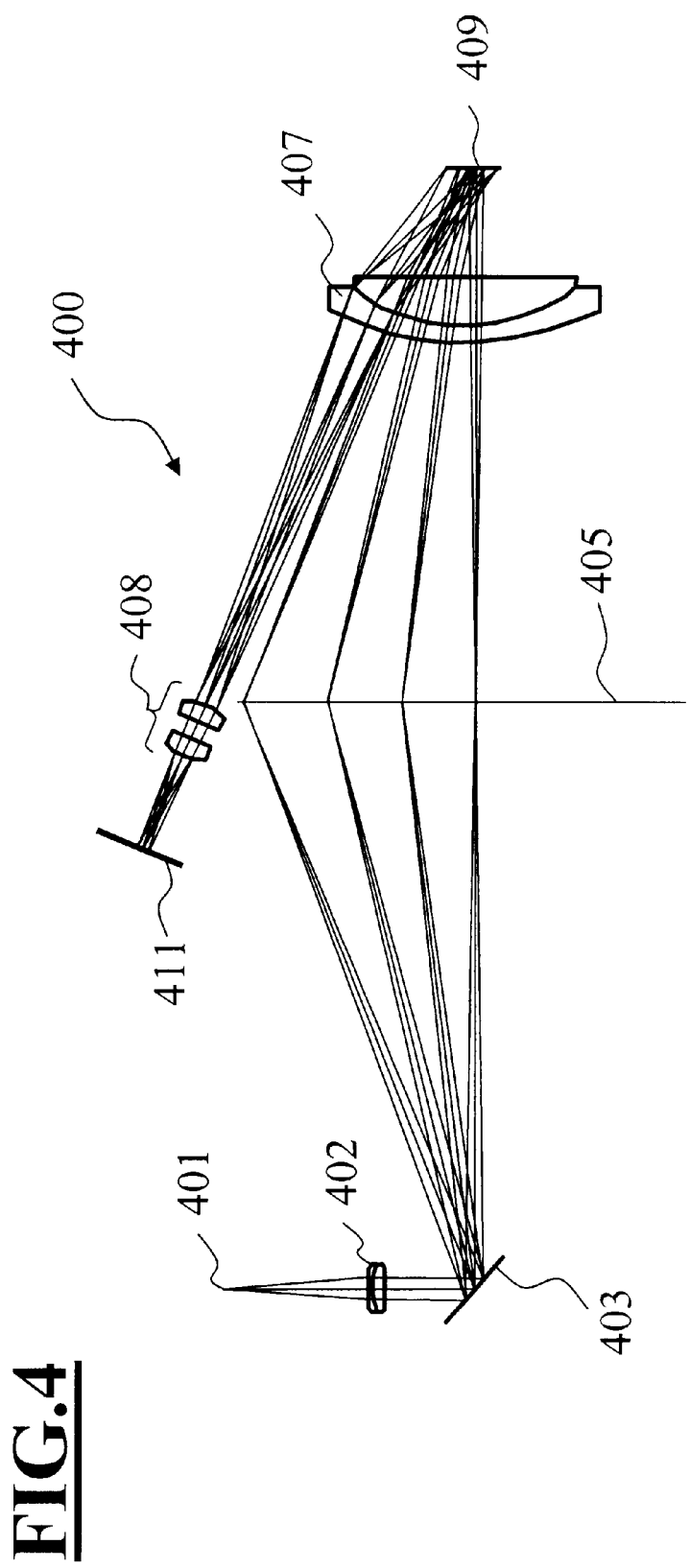
FIG. 4 shows a block diagram of an alternative embodiment of a back projection visual field tester that is fabricated in accordance with the present invention.

FIG. 4 shows a block diagram of back projection visual field tester 400 that is fabricated in accordance with an alternative embodiment of the present invention. For the most part, back projection visual field tester 400 is the same as back projection visual field tester 100 shown in FIG. 1. In particular, light source 401, stimulus projection lens system 402, gimbal-mounted mirror 403, projection screen 405, and magnifier lens system 407 of back projection visual field tester 400 are the same as light source 101, stimulus projection lens system 102, gimbal-mounted mirror 103, projection screen 105, and magnifier lens system 107 of back projection visual field tester 100. A stimulus monitor (for example, photodetector 109 in FIG. 1) and a controller (for example, controller 150 in FIG. 1) may similarly be the same for the two visual field testers. However, as shown in FIG. 4, a patient's test eye plane 409 is imaged to CCD camera 411 through lens system group 408 (although lens system group 408 is shown as being comprised of two lenses, those of ordinary skill in the art will readily understand that lens system group 408 may comprise more lenses) and lens system 407 (although lens system 407 is shown as being comprised of two lenses, those of ordinary skill in the art will readily understand that lens system group 407 may comprise more one or more lenses). Finally, an eye image produced by CCD camera 411 as output may be displayed on a video monitor (not shown in the figure) for monitoring purposes. In addition, as has been disclosed in the prior art, CCD camera 411 can also be used as an eye tracking device either by analyzing a location of the image of the eye in accordance with any one of a number of methods that are well known to those of ordinary skill in the art or by analyzing a reflection of a point light source illumination (not shown) in the figure in accordance with any one of a number of methods that are well known to those of ordinary skill in the art.

Those skilled in the art will recognize that the foregoing description has been presented for the sake of illustration and description only. As such, it is not intended to be exhaustive or to limit the invention to the precise form disclosed.

What is claimed is:

1. A visual field tester comprises:
   a projection screen;
   a stimulus projection system that projects a stimulus from a light source onto a first side of the projection screen;
   a background projection system that projects a substantially uniform background light onto the first side of the projection screen; and
   a magnifier lens system, disposed on a second side of the projection screen, that directs light transmitted through the projection screen to a predetermined location.

2. The visual field tester of claim 1 wherein the stimulus projection system comprises:
   the light source;
   a projection lens system; and a scanner system.

3. The visual field tester of claim 2 wherein the scanner system comprises a gimbal-mounted mirror.

4. The visual field tester of claim 2 wherein the scanner system further comprises a photodetector.

5. The visual field tester of claim 3 wherein the background projection system comprises a source that outputs substantially uniform background light.

6. The visual field tester of claim 1 wherein the stimulus projection system comprises:
   the light source that outputs light;
   an optical fiber system disposed to receive the light output; and
   a projection lens system that projects light output from the optical fiber onto the projection screen.

7. The visual field tester of claim 6 wherein the projection lens system has a predetermined depth of focus that is long enough so that the stimulus is focused over a large area of the projection screen.

8. The visual field tester of claim 7 wherein a numerical aperture of the projection lens system is small enough to achieve the predetermined depth of focus.

9. visual field tester of claim 1 wherein the stimulus projection system comprises:
   the light source having a relatively small aperture that outputs light; and
   a projection lens system that projects light output from the aperture onto the projection screen.

10. The visual field tester of claim 1 wherein the projection screen comprises:
    a lens element; and
    a diffuser element.

11. The visual field tester of claim 10 wherein the lens element comprises a Fresnel lens.

12. The visual field tester of claim 1 wherein the projection screen comprises a holographic diffuser.

13. The visual field tester of claim 1 which further comprises:
    a CCD camera; and
    a lens group to relay light transmitted by the projection screen and reflected, which reflected light is reflected from a patient's eye that is disposed at the predetermined location and which is transmitted through the magnifier lens system, to the CCD camera.

14. The visual field tester of claim 13 that further comprises a monitor that displays an image output from the CCD camera.

15. The visual field tester of claim 1 wherein:
    a blue filter is placed in an optical path of the stimulus projection system to generate a blue stimulus; and
    the background projection system comprises a yellow light source.

16. The visual field tester of claim 15 wherein the yellow light source comprises a yellow LED.

17. The visual field tester of claim 15 wherein the yellow light source comprises a white light source and a yellow filter.

* * * * *